United States Patent [19]

Friese et al.

[11] Patent Number: 5,690,800
[45] Date of Patent: Nov. 25, 1997

[54] ELECTROCHEMICAL MEASURING ELEMENT HAVING A POTENTIAL-FREE SENSOR ELEMENT

[75] Inventors: Karl-Hermann Friese, Leonberg; Frank Stanglmeier, Moeglingen, both of Germany

[73] Assignee: Robeert Bosch GmbH, Stuttgart, Germany

[21] Appl. No.: 687,339
[22] PCT Filed: Nov. 28, 1995
[86] PCT No.: PCT/DE95/01684
  § 371 Date: Aug. 1, 1996
  § 102(e) Date: Aug. 1, 1996
[87] PCT Pub. No.: WO96/21147
  PCT Pub. Date: Jul. 11, 1996

[30] Foreign Application Priority Data

Dec. 31, 1994 [DE] Germany .............. 44 47 306.0

[51] Int. Cl.⁶ ............................ G01N 27/26
[52] U.S. Cl. ........................................ 204/424
[58] Field of Search ........................ 204/424–429

[56] References Cited

U.S. PATENT DOCUMENTS 4,569,748  2/1986  Yamakawa et al. ............ 204/429
5,228,975  7/1993  Yamada et al. ................. 204/424

FOREIGN PATENT DOCUMENTS 4318789  6/1993  Germany.
4342731  12/1993  Germany.

*Primary Examiner*—Bruce F. Bell
*Attorney, Agent, or Firm*—Spencer & Frank

[57] ABSTRACT

Proposed is an electrochemical measuring instrument (10) for determining the oxygen content in gas mixtures, in particular exhaust gases from combustion engines, with a sensor element (14) that is installed potential-free in a metal casing (11). The sensor element (14) has an oxygen ion conducting solid electrolyte body (23) in the shape of a tube closed on one side, with electrodes (25, 26) and connections (27, 28), and is fitted inside the casing (11) with a metal sealing ring (20). The connection (27) which runs along the outer surface of solid electrolyte body (23) is covered with an electrically insulating layer (21), at least in the area surrounding sealing ring (20). In addition, a ductile cover layer (31) that spans solid electrolyte body (23) is applied over insulating layer (21) in the area surrounding sealing ring (20), with which the sensor element (14) rests on sealing ring (20).

9 Claims, 2 Drawing Sheets

ELECTROCHEMICAL MEASURING ELEMENT HAVING A POTENTIAL-FREE SENSOR ELEMENT

This application is a 371 of PCT/DE 95/01684 filed Nov. 28, 1995.

PRIOR ART

The present invention relates to an electrochemical measuring element for determining the oxygen content of gas mixtures.

Electrochemical measuring elements have, for example, a finger-type shape where the solid electrolyte body is fastened tightly inside a metal casing. For finger-type probes, a distinction is made between potential-free and latent potential measuring elements. For latent potential measuring elements, the strip conductor of the outer electrode makes contact with the casing by means of an electrically conducting sealing ring. With the potential-free measuring elements, each electrode connection leads directly to a controller so that no electrical contact with the casing is permitted. A seal between solid electrolyte body and casing must exist in both cases. The solid electrolyte body and the strip conductor of the potential-free probe are covered with an electrically insulating layer where it fits tightly.

ADVANTAGES OF THE INVENTION

The measuring element according to the invention has the advantage that the brittle, electrically insulating layer is protected against pressure points of the metallic sealing ring. This avoids the formation of cracks in the insulating layer which would otherwise have a negative influence on the insulating effect and the mechanical stability of the insulating layer. Because of the deformability of the cover layer, the sealing ring can push into the cover layer so that a closed tight fit results. The measuring element according to the invention additionally leads to increased production safety with regard to gastightness of the sensor element and an improvement in the continuance with regard to the vibration stress for the sensor element/sealing ring arrangement. In addition, the material composition of the cover layer permits the use of commercially available materials and pastes and the use of known application techniques such as, for example, the screen printing technology.

DRAWING

The exemplary embodiments for this invention are shown in the drawing and explained in more detail in the following description. FIG. 1 is a longitudinal cut through the exhaust-gas side of a measuring element according to the invention while FIGS. 2, 3 and 4 each show an enlarged section X according to FIG. 1.

DESCRIPTION OF THE EXEMPLARY EMBODIMENTS

Figure 1:
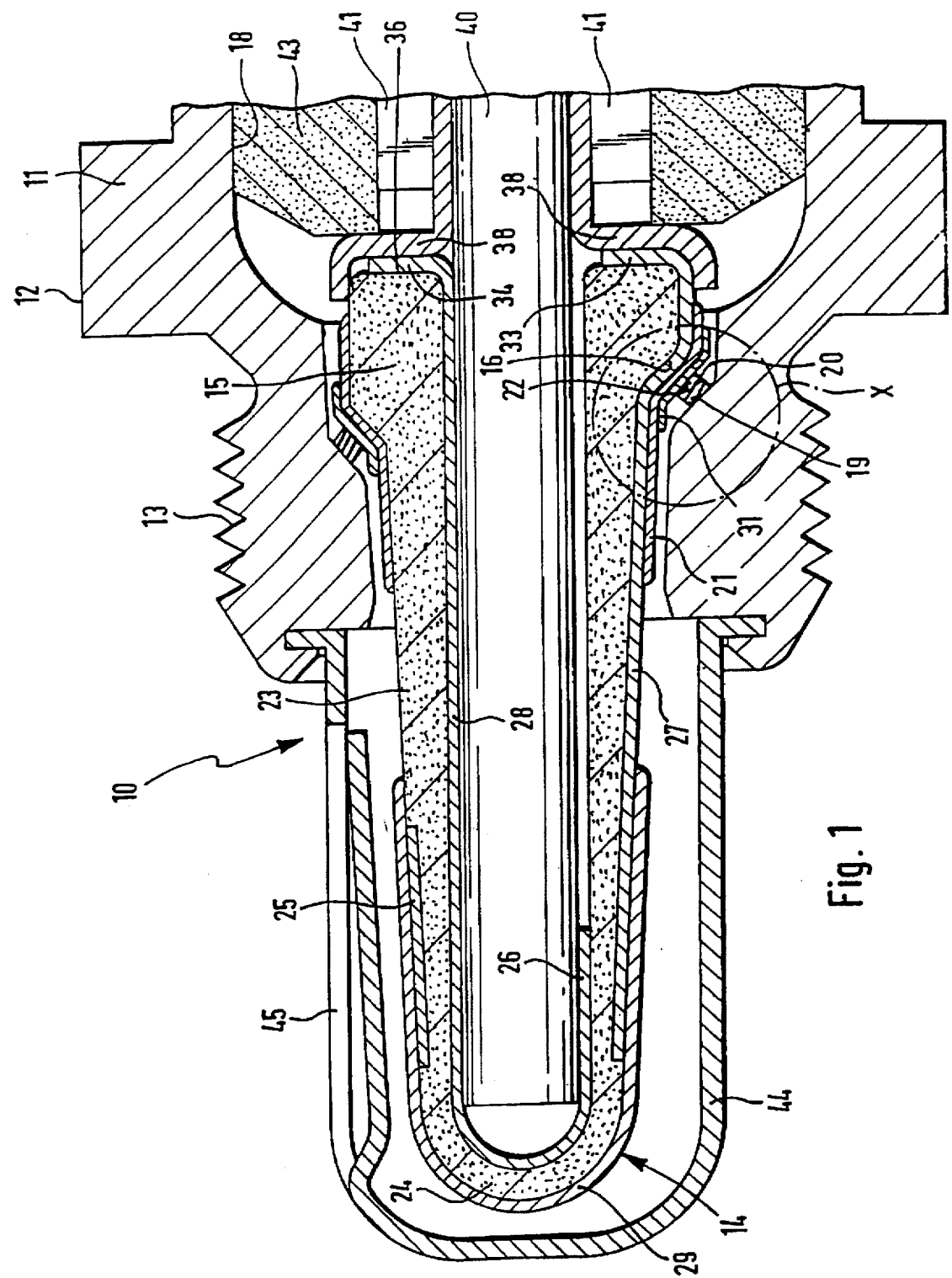

The electrochemical measuring element 10 shown in FIG. 1 has a metal casing 11 with a thread 13 on the outside, used as fastening means, used to install it in a measuring gas tube that is not shown here. Casing 11 has a longitudinal borehole 18 with tight seat 19, onto which is fitted a metal sealing ring 20. A sensor element 14 with a shoulder 16, formed on a toric head 15, sits on tight seat 19 with sealing ring 20. On toric head 15 of the sensor element 14, a sealing surface 22 forms on the sensor element side between sealing ring 20 and sensor element 14. Tight seat 19 also forms a sealing surface on the casing side.

Sensor element 14 has a tube-shaped solid electrolyte body 23, the end section of which is closed on the measuring gas side. On the outside exposed to the measuring gas, a measuring electrode 25 is mounted on the solid electrolyte body 23 while a reference electrode 26, exposed to a reference gas, for example air, is mounted on the side facing toward the inside. Measuring electrode 25 is conducted via a measuring electrode strip conductor 27 to a first electrode contact 33 and the reference electrode 26 is conducted with a reference electrode strip conductor 28 to a second electrode contact 34. The electrode contacts 33, 34 are in each case located on a frontal section 36 that is formed by the open end of solid electrolyte body 23. The measuring electrode is coated with a porous protective layer 29.

Contact piece 38 [sic] rest on the electrode contacts 33, 34. The contact pieces 38 make contact with electrode connectors 41. The electrode connectors 41 lead to a connecting cable that is not shown and which, in turn, leads to a measuring and control mechanism. Furthermore, a ceramic insulating sleeve 43 is fitted into the longitudinal borehole 18 of casing 11. Insulating sleeve 43 is pushed onto contact pieces 38 with the aid of a mechanical means that is not shown.

Sensor element 14, which projects on the measuring gas side from longitudinal borehole 18 of casing 1 [sic], is surrounded at a distance by a protective tube 44 with openings 45 for the intake or exit of the measuring gas and is held in place on the measuring gas side end of casing 11. A rod-shaped heating element 40 is, for example, installed on the sensor element inside.

Figure 2:
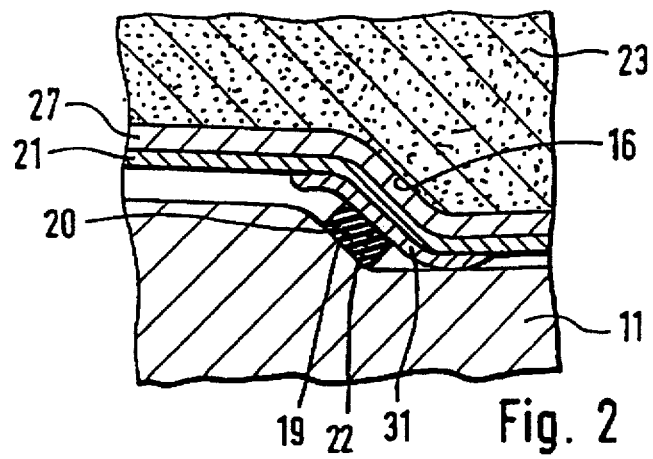

The use of a potential-free sensor element 14 with an electrically conducting sealing ring 20 presupposes that electrodes 25, 26 or strip conductors 27, 28 and the solid electrolyte body are electrically insulated against the metal casing 11. To that effect, the strip conductor 27 is coated in a first exemplary embodiment according to FIG. 2 with an electrically insulating layer 21, in particular in the area of sealing surface 22 on the sensor element side. The insulating layer 21 has a layer thickness of, for example, 20 to 100 µm. A ductile cover layer 31 is placed over the insulating layer 21. The thickness of this cover layer 31 should effectively be selected such that at least the peak-to-valley height of the insulating layer 21 is filled in. It is however preferable if the layer thickness of covering layer 31 is 1.5 times the highest peak-to-valley height of the layer below.

In the exemplary embodiment at hand, the insulating layer 21 stretches over the total area of strip conductor 27, located next to the casing 11. Cover layer 31, for example, extends only slightly over the area of sealing ring 20. However, it is also conceivable to limit insulating layer 21 to the area of sealing ring 20 or sealing surface 22 or to extend insulating layer 21 on the measuring gas side to protective layer 29. On the other hand, it is also conceivable that cover layer 31 is extended to cover the area outside of sealing ring 20 and sealing surface 22, whereby it can also be extended to protective layer 29. However, it is important that cover layer 31 does not come in contact with strip conductor 27 and electrode 25 or solid electrolyte body 23.

Figure 3:
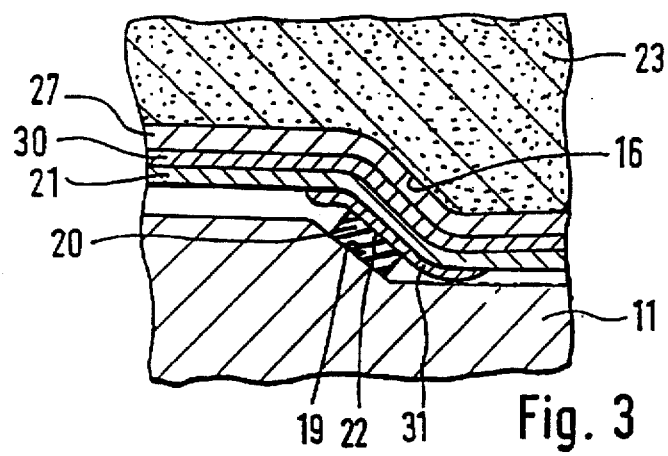

A second exemplary embodiment according to FIG. 3 consists of first coating strip conductor 27 with an undercoating 30, preferably of the solid electrolyte body material, and to apply the insulating layer 21 and cover layer 31 over this in accordance with the already described exemplary embodiment, wherein it makes sense to co-sinter the intermediate coating 30. Undercoating 30 here is designed to prevent the glass-forming material contained in the insulating layer 21 from diffusing into the material for strip conductor 27 and there influence conductivity in a negative way.

According to a first exemplary embodiment, the insulating layer 21 is composed of an electrically insulating ceramic material. The material considered are: $Al_2O_3$, Mg-spinel, Fosterite or a mixture of these materials. According to a second exemplary embodiment, the insulating layer 21 consists of a mixture of a crystalline, non-metallic material and a glass-forming material, wherein the insulating layer 21 during the sintering process forms a glaze packed with the crystalline, non-metallic material. The specific electric resistance of the crystalline, non-metallic material preferably has at least 10 times the specific resistance value of solid electrolyte body 23. The following is considered as crystalline, non-metallic material: $Al_2O_3$, Mg-spinel, Fosterite, MgO-stabilized $ZrO_2$, CaO and/or $Y_2O_3$-stabilized $ZrO_2$ with low stabilizer contents, preferably with maximum ⅔ of the stabilizer oxide of a full stabilization, non-stabilized $ZrO_2$ or $HfO_2$ or a mixture of these materials. The glass-forming material used is an alkaline earth silicate, for example Ba—Al-silicate glass. Up to 30 atomic percentages of barium can be replaced by strontium. The alkaline earth silicate glass can be placed in the form of premelted fritted glass or as glass fiber raw material mixture. The latter is preferably freed for the most part of crystallization water, carbonate or other ignition loss in a calcination process. A small amount (<10 percent in weight) of a glass-forming raw material mixture is preferably added to the fritted glass. The material mixture should not contain more than a maximum 1 percent in weight of electrically conducting impurities, preferably less than 0.2 percent in weight.

Cover layer 31 is composed of temperature stable metals or temperature stable metal alloys wherein the cover layer 31 is a ductile metal layer of pure metals such as palladium, copper, gold, nickel or a like material, or it consists of alloys which do not form intermetallic phases, for example, palladium/nickel, palladium/copper, copper/nickel or a like material. Metal layer 31 is deformable so that sealing ring 20 burrows into metal layer 31 during the insertion of the sensor element, thereby resulting in a tight fit that seals.

The co-sintering of solid electrolyte body 23, insulating layer 21 and cover layer 31 results in a particularly good compound arrangement of cover layer 31, insulating layer 21 and solid electrolyte body 23. However, it is conceivable to apply cover layer 31 to a sintered solid electrolyte body 23. This method is advised with low-melting point metals, e.g. with copper or copper alloys. In that case, insulating layer 21 can also be applied retroactively to the sintered solid electrolyte body 23.

Figure 4:
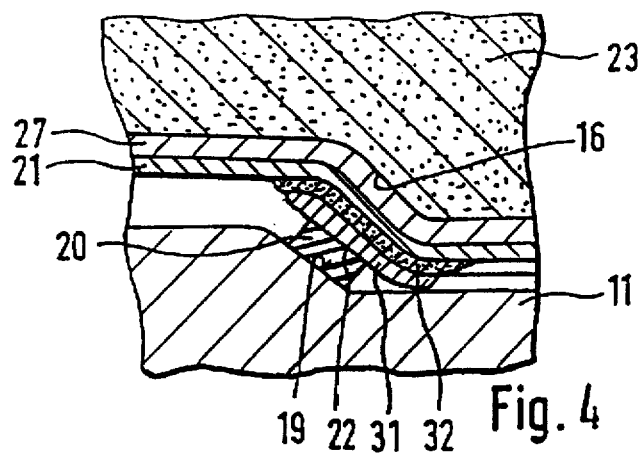

A third embodiment is shown in FIG. 4 where a subbase 32 is placed under cover layer 31, in accordance with the exemplary embodiment in FIG. 1. However, it is also conceivable to place the layers on the sensor element side, in accordance with the exemplary embodiment in FIG. 3. The subbase 32 is a dense ceramic layer, consisting preferably of the material used for solid electrolyte body 23, for example of stabilized $ZrO_2$. To produce a dense layer, the percentage of the fluxing agent for the ceramic base material is selected to be <10%, with no fluxing agent addition producing the densest layer. Subbase 32 itself does not have to have an insulating resistance; rather it can exhibit a noticeable electron and/or ion conductivity. In case of an electrical conductivity, cover layer 31 as well as subbase 32 must not overlap the insulating layer 21. It is useful if subbase 32 has a layer thickness of between 10 to 50 μm.

Furthermore, it has proven advantageous to adapt the thermal expansion coefficient of subbase 32 to approximately $±2×10^{-6}$ $K^{-1}$ to the thermal expansion coefficient of the solid electrolyte body 23.

In the following, various exemplary embodiments for the composition and production of the insulating layer 21 and cover layer 31 are described:

EMBODIMENT 1

In order to produce the insulating layer 21, an inorganic raw material mixture is produced, which consists of 60 percent in weight oxide of aluminum (99.5 percent in weight $Al_2O_3$, <0.1 percent in weight $Na_2O$, specific surface 15 $m^2/g$), 40 percent in weight Ba—Al-silicate glass powder (53 percent in weight BaO, 5 percent in weight $Al_2O_3$, 42 percent in weight $SiO_2$, specific surface 5 $m^2/g$). The raw materials are homogenized and ground for two hours in a ball mill with 90% $Al_2O_3$ grinding balls. Following that, a watery slip is added with 50 g raw material mixture, 500 ml distilled water and 25 ml 10% watery polyvinyl alcohol solution. The slip is ground for a period of 1.5 hours in a ball mill with 90% $Al_2O_3$ grinding balls.

Onto the solid electrolyte body 23, composed of $ZrO_2$ that is, for example, partially stabilized with 5 mol-% $Y_2O_3$ and which has been pre-sintered at 1000° C., the slip is applied to the solid electrolyte body 23 and strip conductor 27 so that the insulating layer 21 forms in accordance with FIG. 1. Subsequently, the slip is dried at, for example, 60° C. Following that, a commercially available 20 μm thick layer of palladium paste with 50 percent in weight Pd (purity 99.9%) is, for example, applied in such a way over the insulating layer 21 that cover layer 31 forms in accordance with FIG. 1. Following that, solid electrolyte body 23, insulating layer 21 and cover layer 31 are co-sintered for approximately 3 hours at 1450° to 1500° C.

EMBODIMENT 2

The slip for insulating layer 21 is applied to solid electrolyte body 23 as described in exemplary embodiment 1. The slip is dried for about 1 hour in the forced-air oven, for example at 120° C. Following that, subbase 32 according to FIG. 4 is applied, which consists of $ZrO_2$ stabilized with 5 mol % $Y_2O_3$. Injection suspensions or printing pastes generally known from prior art are used to generate subbase 32, wherein subbase 32 in the embodiment at hand is brushed on. Subbase 32 is then dried at, for example, 60° C. Subsequently, cover layer 31 is applied in accordance with exemplary embodiment 1 to subbase 32 and the solid electrolyte body 23 with insulating layer 21, subbase 32 and cover layer 31 is co-sintered for approx. 3 hours at 1450° to 1500° C.

EMBODIMENT 3

Insulating layer 21 is formed as described in embodiment 1. Together with the solid electrolyte body 23, insulating layer 21 is sintered at 1450° to 1500° C. Following the sintering operation, a copper paste with 60 percent in weight copper and a layer thickness of, for example, 20 μm is applied as cover layer 31. Subsequently, the copper paste is sinter-fused in a forming gas (90 $N_2$/10 $H_2$) at, for example, 850° C.

EMBODIMENT 4

The insulating layer and the cover layer 31 are formed as described in embodiment 3. However, a copper alloy paste, consisting of 90 percent by volume copper and 2 percent by volume titanium is used for cover layer 31. The sinter-fusing of the copper alloy paste takes place in a moist forming gas with a dew point of, for example, 25° C. The sinter-fusing of the copper alloy past occurs at 850° C.

EMBODIMENT 5

The layer arrangement, consisting of insulating layer 21 and subbase 32, is formed as described in embodiment 2. The cover layer 31 is formed in accordance with the instruction in embodiment 3.

EMBODIMENT 6

The layer arrangement, consisting of insulating layer 21 and subbase 31 [sic]is formed as described in embodiment 3. A copper palladium alloy paste with 50 percent in weight copper and 50 percent in weight palladium is used to form cover layer 31. The sinter-fusing of the copper/palladium alloy paste to the sintered solid electrolyte body 23 occurs, for example, at 900° C.

EMBODIMENT 7

The layer arrangement, consisting of insulating layer 21 and subbase 32 is formed as described in embodiment 3. A gold paste with, for example, 65 percent in weight gold is used to form cover layer 31. The gold paste is sinter-fused to the sintered solid electrolyte body 23 at, for example, 850° C. in air.

EMBODIMENT 8

The layer arrangement with insulating layer 21 and subbase 32 is formed as described in embodiment 3. A gold/copper alloy paste with 95 percent in weight gold and 5 percent in weight copper is used to form cover layer 31. The subsequent sinter-fusing of the gold/copper alloy paste occurs at, for example, 820° C. in air.

We claim:

1. Electrochemical measuring element for determining the oxygen content of gas mixtures in exhaust gases from combustion engines, with a potential-free arranged sensor element, having an oxygen ion conducting solid electrolyte body with electrodes and electrically conducting connections, wherein the sensor element with a sealing ring is inserted into a metal casing and the connection facing the casing is covered with an electrically insulating layer, at least in the area of the sealing ring, characterized in that at least in the area of sealing ring (20), the insulating layer (21) has a ductile cover layer (31), with which the sensor element (14) rests on sealing ring (20).

2. Measuring element according to claim 1, characterized in that the cover layer (31) spans solid electrolyte body (23).

3. Measuring element according to claim 1, characterized in that the cover layer (31) is composed of temperature-stable metals or temperature-stable metal alloys.

4. Measuring element according to claim 3, characterized in that the cover layer (31) from the group consisting of platinum, palladium, copper, gold, titanium, alloys of palladium/nickel, palladium/copper, copper/nickel, copper/titanium and gold/copper.

5. Measuring element according to claim 1, characterized in that the layer thickness of cover layer (31) is at least 1.5 times that of the greatest peak-to-valley height of insulating layer (21).

6. Measuring element according to claim 1, characterized in that the insulating layer (21) consists of an electrically insulating, ceramic material.

7. Measuring element according to claim 1, characterized in that the insulating layer (21) consists of a mixture of a crystalline, non-metallic material and a glass-forming material, such that a glaze filled with the crystalline, non-metallic material forms during the heating up.

8. Measuring element according to claim 1, characterized in that an intermediate layer (30) is placed between the connection (27) and the insulating layer (21), consists of the material for the solid electrolyte body (23).

9. Measuring element according to claim 1, characterized in that on the side of the sensor element, a subbase (32), consisting of the material for solid electrolyte body (23), is placed under the cover layer (31).

* * * * *